US012767623B2

(12) United States Patent
Breidenstein

(10) Patent No.: US 12,767,623 B2
(45) Date of Patent: Oct. 20, 2026

(54) APPARATUS TO PRODUCE HIGH PURITY ETHANOL FROM $CO_2$ AND A LOW BTU GAS STREAM

(71) Applicant: GAS TECHNOLOGIES LLC, Walloon Lake, MI (US)

(72) Inventor: Walter Breidenstein, Boyne Falls, MI (US)

(73) Assignee: GasTechno Corp., Boyne Falls, MI (US)

( * ) Notice: Subject to any disclaimer, the term of this patent is extended or adjusted under 35 U.S.C. 154(b) by 1070 days.

(21) Appl. No.: 17/725,137

(22) Filed: Apr. 20, 2022

(65) Prior Publication Data

US 2022/0332668 A1 Oct. 20, 2022

Related U.S. Application Data

(60) Provisional application No. 63/177,040, filed on Apr. 20, 2021.

(51) Int. Cl.

*C07C 29/152* (2006.01)
*C07C 29/153* (2006.01)
*H05H 1/24* (2006.01)

(52) U.S. Cl.

CPC .......... *C07C 29/152* (2013.01); *C07C 29/153* (2013.01); *H05H 1/2418* (2021.05)

(58) Field of Classification Search

CPC ..... C07C 29/152; C07C 29/153; C07C 29/15; C07C 31/04; C07C 27/06; C07C 2/80; C07C 9/06; C07C 2521/06; C07C 2521/08; H05H 1/2418; H05H 1/2406; H05H 1/2431; H05H 1/2441; Y02P 20/52; C04B 2235/5427; C04B 2111/0081; B01J 35/45; B01J 21/063; B01J 37/036; B01J 19/088; B01J 21/08; B01J 35/64; B01J 35/657; B01J 2219/0875; B01J 2219/0892; B01J 2219/0896; B01J 2219/0815; B01J 23/02; B01J 23/62; B01J 23/52; B01J 5/005; B01J 23/60; B01J 2219/0871

See application file for complete search history.

(56) References Cited

U.S. PATENT DOCUMENTS

| | | | | |
|---|---|---|---|---|
| 9,180,426 | B2 | 11/2015 | Pawlak et al. | |
| 2009/0121637 | A1* | 5/2009 | Laroussi | H05H 1/2406 315/111.21 |
| 2021/0260558 | A1* | 8/2021 | Ha | B01J 21/063 |
| 2021/0275983 | A1* | 9/2021 | Han | C07C 29/15 |

* cited by examiner

*Primary Examiner* — Xiuyu Tai

(74) *Attorney, Agent, or Firm* — Brooks Kushman P.C.

(57) ABSTRACT

Catalytic $CO_2$ hydrogenation to ethanol utilizing radio frequency is very attractive due to higher selectivity (~99%) to ethanol and yield of 0.000718 g/h or higher. A dielectric barrier discharge (DBD) plasma reactor packed with a catalyst comprising of $Cu/Zn/Al_2O_3$ can be used for this purpose, which can be operated at approximately 100-200° C., 1-20 atm pressure and gas flow rates above 20 mL/min. The reactor can be made of a simple inert tube. The process is very attractive for a feasible industrial application. To scale up the process to industrial relevance, a multi-tubular reactor configuration is proposed.

31 Claims, 12 Drawing Sheets

Table 1-1

| | *Unit* | **S-1** | **S-2** | **S-3** | **S-4** | **S-5** | **S-6** |
|---|---|---|---|---|---|---|---|
| | | | | | | | |
| Vapour Fraction | | 1 | 1 | 1 | 1 | 1 | 1 |
| Temperature | *F* | -265 | -7.336257 | -8.54996 | -12.12693 | 100 | -258.7729 |
| Pressure | *psig* | 20 | 1193 | 12 | 14 | 2600 | 1191 |
| Molar Flow | *lb-mole/hr* | 1.030609 | 19.63545 | 10.63213 | 10.63213 | 40.2386 | 0 |
| Mass Flow | *lb/hr* | 22.45261 | 331.9362 | 464.6742 | 464.6742 | 1072.923 | 0 |
| Liquid Volume Flow | *barrel/day* | 3.142108 | 70.21998 | 38.71013 | 38.71013 | 145.022 | 0 |
| Heat Flow | *Btu/hr* | -20543.71 | -622338.1 | -1781374 | -1781745 | -3297876 | 0 |
| Std Gas Flow | *MSCFD* | 9.368249 | 178.4865 | 96.6462 | 96.6462 | 365.7695 | 0 |
| | | | | | | | |
| Comp Mole Frac (CO2) | | 0.0001% | 0.0123% | 98.2285% | 98.2285% | 36.0366% | 0.0123% |
| Comp Mole Frac (H2S) | | 0.0000% | 0.0000% | 0.7126% | 0.7126% | 0.3206% | 0.0000% |
| Comp Mole Frac (Oxygen) | | 5.4208% | 1.8684% | 0.0566% | 0.0566% | 1.1037% | 1.8684% |
| Comp Mole Frac (Nitrogen) | | 40.7483% | 4.6665% | 0.1649% | 0.1649% | 2.5471% | 4.6665% |
| Comp Mole Frac (Methane) | | 53.8308% | 93.4414% | 0.6093% | 0.6093% | 59.8175% | 93.4414% |
| Comp Mole Frac (Methanol) | | 0.0000% | 0.0104% | 0.2013% | 0.2013% | 0.0022% | 0.0104% |
| Comp Mole Frac (H2O) | | 0.0000% | 0.0008% | 0.0269% | 0.0269% | 0.1723% | 0.0008% |

*Fig. 6A*

Table 1-2

| | *Unit* | **S-8** | **S-9** | **S-10** | **S-11** | **S-12** |
|---|---|---|---|---|---|---|
| | | | | | | |
| Vapour Fraction | | 0 | 0 | 0 | 0 | 0.248087066 |
| Temperature | *F* | -258.7729 | -258.7729 | -16 | -256.108064 | 58.34688169 |
| Pressure | *psig* | 1191 | 1191 | 797 | 600 | 796 |
| Molar Flow | *lbmole/hr* | 19.63545 | 19.63545 | 18.6 | 19.63544616 | 18.6 |
| Mass Flow | *lb/hr* | 331.9362 | 331.9362 | 802.1188 | 331.936211 | 802.1188251 |
| Liquid Volume Flow | *barrel/day* | 70.21998 | 70.21998 | 67.83356 | 70.21997698 | 67.83356415 |
| Heat Flow | *Btu/hr* | -710910.5 | -710910.5 | -3191869 | -710910.508 | -3139830.12 |
| Std Gas Flow | *MSCFD* | 178.4865 | 178.4865 | 169.0743 | 178.4864875 | 169.074267 |
| | | | | | | |
| Comp Mole Frac (CO2) | | 0.0123% | 0.0123% | 96.5427% | 0.0123% | 96.5427% |
| Comp Mole Frac (H2S) | | 0.0000% | 0.0000% | 0.0765% | 0.0000% | 0.0765% |
| Comp Mole Frac (Oxygen) | | 1.8684% | 1.8684% | 0.0296% | 1.8684% | 0.0296% |
| Comp Mole Frac (Nitrogen) | | 4.6665% | 4.6665% | 0.0354% | 4.6665% | 0.0354% |
| Comp Mole Frac (Methane) | | 93.4414% | 93.4414% | 2.9492% | 93.4414% | 2.9492% |
| Comp Mole Frac (Methanol) | | 0.0104% | 0.0104% | 0.3666% | 0.0104% | 0.3666% |
| Comp Mole Frac (H2O) | | 0.0008% | 0.0008% | 0.0000% | 0.0008% | 0.0000% |

*Fig. 6B*

Table 1-3

| | *Unit* | **S-13** | **S-14** | **S-15** | **S-16** | **S-17** | **S-18** |
|---|---|---|---|---|---|---|---|
| | | | | | | | |
| Vapour Fraction | | 0 | 0 | 0 | 1 | 0 | 0.033957 |
| Temperature | *F* | -10.9402545 | -20 | -256.1081 | -6.85780648 | -6.85780648 | -12.12693 |
| Pressure | *psig* | 1200 | 1200 | 600 | 400 | 400 | 14 |
| Molar Flow | *lbmole/hr* | 302.4766279 | 300 | 19.63545 | 7.494400997 | 313.1087567 | 313.1088 |
| Mass Flow | *lb/hr* | 7615.723643 | 7508.629 | 331.9362 | 169.2178378 | 8080.397853 | 8080.398 |
| Liquid Volume Flow | *barrel/day* | 607.8644415 | 598.9928 | 70.21998 | 27.22018431 | 646.5745667 | 646.5746 |
| Heat Flow | *Btu/hr* | -35250456.5 | - 34198310 | -710910.5 | -472564.799 | -37071744.4 | - 37071744 |
| Std Gas Flow | *MSCFD* | 2749.51689 | 2727.004 | 178.4865 | 68.12421265 | 2846.163093 | 2846.163 |
| | | | | | | | |
| Comp Mole Frac ($CO_2$) | | 0.7893% | 0.0000% | 0.0123% | 22.2440% | 4.0980% | 4.0980% |
| Comp Mole Frac ($H_2S$) | | 0.0155% | 0.0000% | 0.0000% | 0.0840% | 0.0392% | 0.0392% |
| Comp Mole Frac (Oxygen) | | 0.0000% | 0.0000% | 1.8684% | 0.9499% | 0.0019% | 0.0019% |
| Comp Mole Frac (Nitrogen) | | 0.0000% | 0.0000% | 4.6665% | 1.2146% | 0.0056% | 0.0056% |
| Comp Mole Frac (Methane) | | 0.0000% | 0.0000% | 93.4414% | 75.4869% | 0.0207% | 0.0207% |
| Comp Mole Frac (Methanol) | | 49.5827% | 50.0000% | 0.0104% | 0.0189% | 47.9058% | 47.9058% |
| Comp Mole Frac (H2O) | | 49.6125% | 50.0000% | 0.0008% | 0.0017% | 47.9287% | 47.9287% |

*Fig. 6C*

Table 1-4

| | *Unit* | **S-19** | **S-20** | **S-21** | **S-21+** | **S-22** | **S-23** | **S-24** |
|---|---|---|---|---|---|---|---|---|
| | | | | | | | | |
| Vapour Fraction | | 1 | 1 | 0.993701 | 1 | 0 | 0.967350626 | 1 |
| Temperature | *F* | -47.83094 | 90.70304 | 100 | -47.8298428 | 29.12503024 | -22.2420341 | 27.12476 |
| Pressure | *psig* | 14 | 0.29 | 2600 | 14 | 2599 | 1200 | 13 |
| Molar Flow | *lbmole/hr* | 7.494401 | 40.49366 | 40.49366 | 7.493664965 | 40.23860382 | 40.23860382 | 7.493665 |
| Mass Flow | *lb/hr* | 169.2178 | 1077.594 | 1077.594 | 169.2008706 | 1072.9234 | 1072.9234 | 169.2009 |
| Liquid Volume Flow | *barrel/day* | 27.22018 | 145.3444 | 145.3444 | 27.21748579 | 145.0219567 | 145.0219567 | 27.21749 |
| Heat Flow | *Btu/hr* | -472564.8 | -3260274 | -3329227 | -472514.888 | -3349915.73 | -3354610.22 | -467820.4 |
| Std Gas Flow | *MSCFD* | 68.12421 | 368.088 | 368.088 | 68.1175221 | 365.7694863 | 365.7694863 | 68.11752 |
| | | | | | | | | |
| Comp Mole Frac (CO2) | | 22.2440% | 35.8160% | 35.8160% | 22.2437% | 36.0366% | 36.0366% | 22.2437% |
| Comp Mole Frac (H2S) | | 0.0840% | 0.3187% | 0.3187% | 0.0840% | 0.3206% | 0.3206% | 0.0840% |
| Comp Mole Frac (Oxygen) | | 0.9499% | 1.0967% | 1.0967% | 0.9500% | 1.1037% | 1.1037% | 0.9500% |
| Comp Mole Frac (Nitrogen) | | 1.2146% | 2.5311% | 2.5311% | 1.2147% | 2.5471% | 2.5471% | 1.2147% |
| Comp Mole Frac (Methane) | | 75.4869% | 59.4407% | 59.4407% | 75.4870% | 59.8175% | 59.8175% | 75.4870% |
| Comp Mole Frac (Methanol) | | 0.0189% | 0.0035% | 0.0035% | 0.0189% | 0.0022% | 0.0022% | 0.0189% |
| Comp Mole Frac (H2O) | | 0.0017% | 0.7933% | 0.7933% | 0.0017% | 0.1723% | 0.1723% | 0.0017% |

*Fig. 6D*

Table 1-5

| | *Unit* | **S-25** | **S-26** | **S-29** | **S-30** | **S-31** | **S-32** |
|---|---|---|---|---|---|---|---|
| | | | | | | | |
| Vapour Fraction | | 0 | 0 | 0 | 1 | 1 | 0.052627 |
| Temperature | *F* | 23.24972 | 100 | -256.350094 | -257.108 | -265 | -264.9862 |
| Pressure | *psig* | 2598 | 2600 | 599 | 19 | 20 | 20 |
| Molar Flow | *lb-mole/hr* | 40.2386 | 0.255061 | 19.63544616 | 1.030609 | 1.030609 | 19.63545 |
| Mass Flow | *lb/hr* | 1072.923 | 4.67037 | 331.936211 | 22.45261 | 22.45261 | 331.9362 |
| Liquid Volume Flow | *barrel/day* | 145.022 | 0.322402 | 70.21997698 | 3.142108 | 3.142108 | 70.21998 |
| Heat Flow | *Btu/hr* | -3354610 | -31350.15 | -710974.1 | -20480.12 | -20543.71 | -710974.1 |
| Std Gas Flow | *MSCFD* | 365.7695 | 2.31851 | 178.4864875 | 9.368249 | 9.368249 | 178.4865 |
| | | | | | | | |
| Comp Mole Frac (CO2) | | 36.0366% | 1.0042% | 0.0123% | 0.0001% | 0.0001% | 0.0123% |
| Comp Mole Frac (H2S) | | 0.3206% | 0.0230% | 0.0000% | 0.0000% | 0.0000% | 0.0000% |
| Comp Mole Frac (Oxygen) | | 1.1037% | 0.0008% | 1.8684% | 5.4208% | 5.4208% | 1.8684% |
| Comp Mole Frac (Nitrogen) | | 2.5471% | 0.0051% | 4.6665% | 40.7483% | 40.7483% | 4.6665% |
| Comp Mole Frac (Methane) | | 59.8175% | 0.0001% | 93.4414% | 53.8308% | 53.8308% | 93.4414% |
| Comp Mole Frac (Methanol) | | 0.0022% | 0.2150% | 0.0104% | 0.0000% | 0.0000% | 0.0104% |
| Comp Mole Frac (H2O) | | 0.1723% | 98.7519% | 0.0008% | 0.0000% | 0.0000% | 0.0008% |

*Fig. 6E*

Table 1-6

| | *Unit* | **S-100** | **S-101** | **S-107** | **S-112** | **S-113** | **S-114** |
|---|---|---|---|---|---|---|---|
| Vapour Fraction | | 1 | 1 | 1 | 0 | 0 | 0 |
| Temperature | *F* | 105 | 2362.945 | -5.756332 | -265 | -259.773047 | -259.773047 |
| Pressure | *psig* | 0.29 | 2600 | 1195 | 20 | 800 | 800 |
| Molar Flow | *lbmole/hr* | 33 | 40.49366 | 19.63545 | 18.60484 | 18.60483736 | 18.60483736 |
| Mass Flow | *lb/hr* | 908.3929 | 1077.594 | 331.9362 | 309.4836 | 309.4836055 | 309.4836055 |
| Liquid Volume Flow | *barrel/day* | 118.1269 | 145.3444 | 70.21998 | 67.07787 | 67.0778686 | 67.0778686 |
| Heat Flow | *Btu/hr* | -2792454 | -1934779 | -621967.9 | -690442.3 | -688300.987 | -688300.987 |
| Std Gas Flow | *MSCFD* | 299.9705 | 368.088 | 178.4865 | 169.1182 | 169.1182387 | 169.1182387 |
| | | | | | | | |
| Comp Mole Frac (CO2) | | 38.8980% | 35.8160% | 0.0123% | 0.0130% | 0.0130% | 0.0130% |
| Comp Mole Frac (H2S) | | 0.3720% | 0.3187% | 0.0000% | 0.0000% | 0.0000% | 0.0000% |
| Comp Mole Frac (Oxygen) | | 1.1300% | 1.0967% | 1.8684% | 1.6716% | 1.6716% | 1.6716% |
| Comp Mole Frac (Nitrogen) | | 2.8301% | 2.5311% | 4.6665% | 2.6678% | 2.6678% | 2.6678% |
| Comp Mole Frac (Methane) | | 55.7969% | 59.4407% | 93.4414% | 95.6356% | 95.6356% | 95.6356% |
| Comp Mole Frac (Methanol) | | 0.0000% | 0.0035% | 0.0104% | 0.0110% | 0.0110% | 0.0110% |
| Comp Mole Frac (H2O) | | 0.9730% | 0.7933% | 0.0008% | 0.0009% | 0.0009% | 0.0009% |
| | | | | | | | |

*Fig. 6F*

Table 1-7

| | *Unit* | **S-201** | **S-202+** | **S-202-** | **CO2 vent gas mix** | **S-rich** | **Purified methane** | **S-scrub** |
|---|---|---|---|---|---|---|---|---|
| | | | | | | | | |
| Vapour Fraction | | 0.000985108 | 0.023376 | 0.014941 | 1 | 1 | 0.999996 | 0 |
| Temperature | *F* | -8.49852024 | -6.857806 | -6.857806 | -12.12693 | -265 | -18.0878 | -12.1269 |
| Pressure | *psig* | 1200 | 400 | 400 | 14 | 20 | 798 | 14 |
| Molar Flow | *lbmole/hr* | 320.6031577 | 320.6032 | 320.6032 | 10.63213 | 1.0306088 | 18.60484 | 302.4766 |
| Mass Flow | *lb/hr* | 8249.615691 | 8249.616 | 8249.616 | 464.6742 | 22.45260552 | 309.4836 | 7615.724 |
| Liquid Volume Flow | *barrel/day* | 673.7947511 | 673.7948 | 673.7948 | 38.71013 | 3.142108373 | 67.07787 | 607.8644 |
| Heat Flow | *Btu/hr* | -36905800.8 | -37544309 | -36905800 | -1781745 | -20543.7147 | -599729 | -3.5E+07 |
| Std Gas Flow | *MSCFD* | 2914.287305 | 2914.287 | 2914.287 | 96.6462 | 9.368248786 | 169.1182 | 2749.517 |
| | | | | | | | | |
| Comp Mole Frac (CO2) | | 4.5222% | 4.5222% | 4.5222% | 98.2285% | 0.0001% | 0.00013 | 0.007893 |
| Comp Mole Frac (H2S) | | 0.0402% | 0.0402% | 0.0402% | 0.7126% | 0.0000% | 2.27E-09 | 0.000155 |
| Comp Mole Frac (Oxygen) | | 0.0241% | 0.0241% | 0.0241% | 0.0566% | 5.4208% | 0.016716 | 3.62E-08 |
| Comp Mole Frac (Nitrogen) | | 0.0339% | 0.0339% | 0.0339% | 0.1649% | 40.7483% | 0.026678 | 2.58E-07 |
| Comp Mole Frac (Methane) | | 1.7848% | 1.7848% | 1.7848% | 0.6093% | 53.8308% | 0.956356 | 4.98E-08 |
| Comp Mole Frac (Methanol) | | 46.7864% | 46.7864% | 46.7864% | 0.2013% | 0.0000% | 0.00011 | 0.495827 |
| Comp Mole Frac (H2O) | | 46.8084% | 46.8084% | 46.8084% | 0.0269% | 0.0000% | 8.85E-06 | 0.496125 |

*Fig. 6G*

APPARATUS TO PRODUCE HIGH PURITY ETHANOL FROM $CO_2$ AND A LOW BTU GAS STREAM

CROSS-REFERENCE TO RELATED APPLICATIONS

This application claims the benefit of U.S. provisional application Ser. No. 63/177,040, filed Apr. 20, 2021, the disclosure of which is hereby incorporated in its entirety by reference herein.

TECHNICAL FIELD

In at least one aspect, a system for converting carbon dioxide to ethanol with integrated zero emission power generation is provided.

BACKGROUND $CO_2$ emission from the combustion of fossil fuel reached about 37.1 Gt in 2018. Since $CO_2$ is a greenhouse gas (GHG), an increase in $CO_2$ concentration is linked to the global temperature rise and business as usual will lead to an increase of temperature about 1.5° C. and climate change [1]. Therefore, carbon capture, utilization, and storage (CCUS) are considered to be the technical and economically viable methods to lower GHG emissions. Currently, there are various CCUS technologies available that depend on the cost of installation, flue gas composition, and properties, desired purity, etc. Chemical absorption, physical absorption, membrane separation, calcium looping, chemical looping, and oxy-fuel separation are the major CCUS technologies, to name a few that are currently being used globally on an industrial scale.

The Intergovernmental Panel on Climate Change (IPCC) fifth assessment report set a target to keep $CO_2$ concentration below 450 ppm by 2021[2]. The current installed CCUS capacity around the world is about 40 Mt of $CO_2$ per year, which is about 0.1% of the net $CO_2$ emission globally. The current $CO_2$ concentration in the atmosphere is about 416 ppm, and an increasing trend is observed for the last few decades. Therefore, new routes of carbon utilization have to be developed that can capture the $CO_2$ to fuels, chemicals, and building materials. It is estimated that these alternative routes have the potential to consume about 5 $GtCO_2$ per year.

Chemical conversion of $CO_2$ to alcohols such as methanol and ethanol are very attractive as liquids are easy to transport and store. More importantly, alcohols are defined as advanced fuels and can also be used as fuel additives and solvents, thereby making them an important commodity in today's market.

Large-scale production of methanol is achieved industrially by catalytic reaction of carbon monoxide and hydrogen gas mixture, also known as syngas. The syngas is commercially produced by different routes such as steam methane reforming, partial oxidation of methane, auto thermal reforming. Alternatively, $CO_2$ reforming of methane, also known as dry reforming of methane (DRM), is trending in order to enhance $CO_2$ utilization. However, due to several technical challenges associated with the DRM process, it was never commercialized, and it remains a subject of academic research as it requires the cost-effective utilization of $CO_2$.

Ethanol is traditionally produced from the formation of sugar. Both corn and sugar cane are major feedstocks for the industrial production of ethanol on the North and South American continents.

Recently, $CO_2$ has been identified as a potential feedstock for the production of ethanol. The chemical conversion of $CO_2$ to ethanol can be achieved by highly selective catalytic processes that could be very useful to convert any known sources of $CO_2$ of sufficient quantity such as flu or vent gas from many industries where high purity $CO_2$ streams are released into the atmosphere. Catalysts comprising iron and potassium have been reported to show high selectivity (~80%) to ethanol. However, due to the requirement of intense capital costs and operating costs, conventional catalytic hydrogenation of $CO_2$ has not matured into a commercial success.

Alternatively, recent advances in electrochemistry in the field of $CO_2$ reduction reaction ($CO_2RR$) to valuable chemicals have enabled engineers to achieve higher efficiency. Electrochemical $CO_2RR$ to hydrocarbon fuels and chemicals offers a carbon neutral or carbon negative strategy, and is a very attractive CCUS technology. However, the design of novel electrocatalyst and the electrolyzer are the major obstacles as well as increasing the Faradaic efficiency (FE) for the $CO_2RR$. Electrochemical $CO_2RR$ to ethanol can be developed on supported metal catalyst, specifically on a Cu-based catalyst. The state-of-the-art technology in the electrochemical $CO_2RR$ to ethanol pathway has been reached by a FE of about 91%, which translates into a yield of 0.000781 g/h. However, the stability of the electrocatalyst is still limited to 16 h, which inhibits the industrial application [3].

SUMMARY

In at least one aspect, a plasma reactor system for producing ethanol from carbon dioxide is provided. The plasma reactor system includes one or more dielectric barrier discharge plasma reactors. Each dielectric barrier discharge plasma reactor is packed with a transition metal oxide catalyst. Characteristically, the dielectric barrier discharge plasma reactors are adapted to receive a plasma reactor gas feed from an industrial reactor and output ethanol.

In some aspects, catalytic $CO_2$ hydrogenation to ethanol utilizing radio frequency is very attractive due to the easy scale-up, higher selectivity (~99%) to ethanol, and comparable yield of 0.000718 g/h. A dielectric barrier discharge (DBD) plasma reactor packed with catalyst comprising of $Cu/Zn/Al_2O_3$ can be used for this purpose, which can be operated at approximate ranges of 100-200° C., 1-20 atm pressure and gas flow rates more than 20 mL/min. Since the process conditions are moderate, and the reactor can be made of a simple inert tube, the process is incredibly attractive for a feasible industrial application. A multi-tubular reactor configuration, whether in parallel or series, will enable higher volumes of the gas conversion per pass while utilizing heat integration among the reactors. The catalysts are available commercially and considered stable for long-term operations without any major downtime in contrast to the traditional 16 h limitation of the electrochemical process.

In another aspect, an oxygen source includes a generator that separates oxygen and nitrogen from air to provide an oxygen stream and a gaseous nitrogen stream and a flow-driven generator that is operated by the flow of the gaseous nitrogen stream to generate electricity.

In another aspect, an industrial reactor system that can provide $CO_2$ to the plasma reactors disclosed wherein is provided. The industrial reactor system includes a first stage and a second stage. The first stage separates a discharge stream and a purified methane-containing gas stream from an input from a methane-containing source gas stream. Characteristically, the discharge composition includes carbon dioxide, hydrogen sulfide, and water. The second stage produces liquid natural gas purified methane-containing gas from the purified methane-containing gas stream.

In another aspect, the first stage includes gas-liquid separator that separates $CO_2$ from the discharge stream.

In another aspect, the second stage includes a gas-liquid separator that separates liquid methane from the purified methane-containing gas stream.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

For a further understanding of the nature, objects, and advantages of the present disclosure, reference should be had to the following detailed description, read in conjunction with the following drawings, wherein like reference numerals denote like elements and wherein:

FIGS. 6A, 6B, 6C, 6D, 6E, 6F, and 6G. Table 1 providing physical and compositional properties of the streams in the reactor system of FIG. 5.

DETAILED DESCRIPTION

Figure 1:
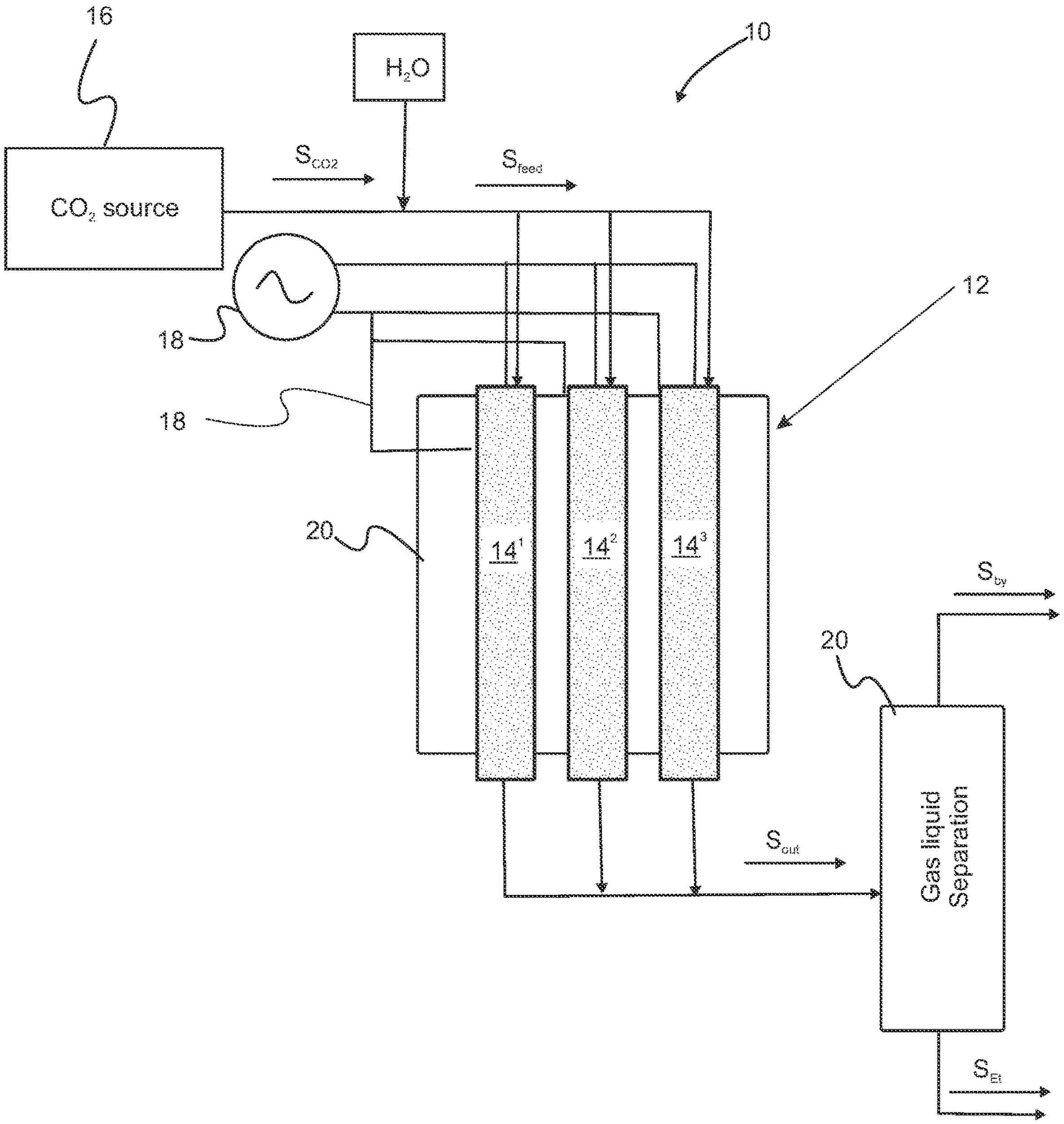
FIG. 1. Multi-tubular plasma reactor with GASTECHNO $CO_2$ separation design.

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It must also be noted that, as used in the specification and the appended claims, the singular form "a," "an," and "the" comprise plural referents unless the context clearly indicates otherwise. For example, reference to a component in the singular is intended to comprise a plurality of components.

As used herein, the term "about" means that the amount or value in question may be the specific value designated or some other value in its neighborhood. Generally, the term "about" denoting a certain value is intended to denote a range within +/−5% of the value. As one example, the phrase "about 100" denotes a range of 100+/−5, i.e. the range from 95 to 105. Generally, when the term "about" is used, it can be expected that similar results or effects according to the invention can be obtained within a range of +/−5% of the indicated value.

As used herein, the term "hand/or" means that either all or only one of the elements of said group may be present. For example, "A and/or B" shall mean "only A, or only B, or both A and B". In the ease of "only A", the term also covers the possibility that B is absent, i.e. "only A, but not B".

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

The phrase "composed of" means "including" or "consisting of" Typically, this phrase is used to denote that an object is formed from a material.

With respect to the terms "comprising," "consisting of," and "consisting essentially of," where one of these three terms is used herein, the presently disclosed and claimed subject matter can include the use of either of the other two terms.

The term "one or more" means "at least one" and the term "at least one" means "one or more." The terms "one or more" and "at least one" include "plurality" and "multiple" as a subset. In a refinement, "one or more" includes "two or more."

The term "substantially," "generally," or "about" may be used herein to describe disclosed or claimed embodiments. The term "substantially" may modify a value or relative characteristic disclosed or claimed in the present disclosure. In such instances, "substantially" may signify that the value or relative characteristic it modifies is within ±0%, 0.1%, 0.5%, 1%, 2%, 3%, 4%, 5% or 10% of the value or relative characteristic.

It should also be appreciated that integer ranges explicitly include all intervening integers. For example, the integer range 1-10 explicitly includes 1, 2, 3, 4, 5, 6, 7, 8, 9, and 10. Similarly, the range 1 to 100 includes 1, 2, 3, 4 . . . 97, 98, 99, 100. Similarly, when any range is called for, intervening numbers that are increments of the difference between the upper limit and the lower limit divided by 10 can be taken as alternative upper or lower limits. For example, if the range is 1.1. to 2.1 the following numbers 1.2, 1.3, 1.4, 1.5, 1.6, 1.7, 1.8, 1.9, and 2.0 can be selected as lower or upper limits.

In the figures for reactor, lines represent conduits. Component connected by lines are in fluid communication. In a series of components connected by lines, all of the components are in fluid communication with each other.

When referring to a numeral quantity, in a refinement, the term "less than" includes a lower non-included limit that is 5 percent of the number indicated after "less than." For example, "less than 20" includes a lower non-included limit of 1 in a refinement. Therefore, this refinement of "less than 20" includes a range between 1 and 20. In another refinement, the term "less than" includes a lower non-included limit that is, in increasing order of preference, 20 percent, 10 percent, 5 percent, or 1 percent of the number indicated after "less than."

In the examples set forth herein, concentrations, temperature, and reaction conditions (e.g., pressure, pH, flow rates, etc.) can be practiced with plus or minus 50 percent of the values indicated rounded to or truncated to two significant figures of the value provided in the examples. In a refinement, concentrations, temperature, and reaction conditions (e.g., pressure, pH, flow rates, etc.) can be practiced with plus or minus 30 percent of the values indicated rounded to or truncated to two significant figures of the value provided in the examples. In another refinement, concentrations, temperature, and reaction conditions (e.g., pressure, pH, flow rates, etc.) can be practiced with plus or minus 10 percent of the values indicated rounded to or truncated to two significant figures of the value provided in the examples.

For all compounds expressed as an empirical chemical formula with a plurality of letters and numeric subscripts (e.g., $CH_2O$), values of the subscripts can be plus or minus 50 percent of the values indicated rounded to or truncated to two significant figures. For example, if $CH_2O$ is indicated, a compound of formula $C_{(0.8-1.2)}H_{(1.6-2.4)}O_{(0.8-1.2)}$. In a refinement, values of the subscripts can be plus or minus 30 percent of the values indicated rounded to or truncated to two significant figures. In still another refinement, values of the subscripts can be plus or minus 20 percent of the values indicated rounded to or truncated to two significant figures.

The term "transition metal" means an element whose atom has a partially filled d sub-shell, or which can give rise to cations with an incomplete d sub-shell. Examples of transition metals include scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum, and gold.

The term "p-block" means elements in groups 13 to 18 of the Periodic Table with a general electronic configuration of $ns^2 np^{1-6}$.

Throughout this application, where publications are referenced, the disclosures of these publications in their entireties are hereby incorporated by reference into this application to more fully describe the state of the art to which this invention pertains.

Abbreviations:

"BTU" means British thermal unit.

"DBD" means dielectric barrier discharge.

"GTL" means gas to liquids.

"LNG" means liquid natural gas.

"MSCFD" means million standard cubic feet per day.

"NG" means natural gas.

"RF" means radio frequency.

Referring to FIG. 1, a schematic of a multi-tubular plasma reactor system with GASTECHNO $CO_2$ separation design is provided. Plasma reactor system 10 includes $CO_2$ conversion system 12 that includes a plurality of dielectric barrier discharge plasma reactors 14$^i$ where i is an integer label for each reactor. Although virtually any number of dielectric barrier discharge plasma reactors can be used, typically $CO_2$ conversion subsystem 12 includes 1 to 50 dielectric barrier discharge plasma reactors 14$^i$. FIG. 1 depicts an example with 3 dielectric barrier discharge plasma reactors (i.e., i=3). A $CO_2$-containing gas feed stream $S_{feed}$ is provided to $CO_2$ conversion subsystem 12. $CO_2$-containing gas feed stream $S_{feed}$ includes $CO_2$-containing gas stream $S_{CO2}$ from a CO2 source 16. If the water content of $CO_2$-containing gas stream $S_{CO2}$ is insufficient, water is added to $CO_2$-containing gas stream $S_{CO2}$ to form $CO_2$-containing gas feed stream $S_{feed}$. If the water content of $CO_2$-containing gas stream $S_{CO2}$ is sufficient, $CO_2$-containing gas stream $S_{CO2}$ can operate as the $CO_2$-containing gas feed stream $S_{feed}$. The $CO_2$ source 16 can be virtually any source of $CO_2$ including industrial reactors and naturally occurring sources of $CO_2$. In a refinement, the $CO_2$-containing source is an industrial reactor produced methanol, ethanol, or combinations thereof.

The plurality of dielectric barrier discharge plasma reactors 14$^i$ converts the $CO_2$-containing gas stream $S_{CO2}$ into an output ethanol-containing stream $S_{Et}$. Power supply 18 is used to power the electrodes contained in the dielectric barrier discharge plasma reactors 14$^i$. The outputs from all of the dielectric barrier discharge plasma reactors 14$^i$. are pooled to form output ethanol-containing stream $S_{out}$. Gas-liquid separator 20 is used to separate ethanol as stream $S_{Et}$ from other reaction byproducts and impurities as stream $S_{by}$. In a refinement, the proprietary purge gas stream of the GASTECHNO® process set forth below is integrated with a plasma reactor system 10 for highly economical and efficient production of high purity ethanol.

A plasma in reactors can be thermally and/or non-thermally generated. Sources of power can be from both non-renewable or renewable sources such as methane, associated gases, nitrogen, carbon dioxide, wind, solar, hydro, nuclear or a combination thereof.

Figure 2A:
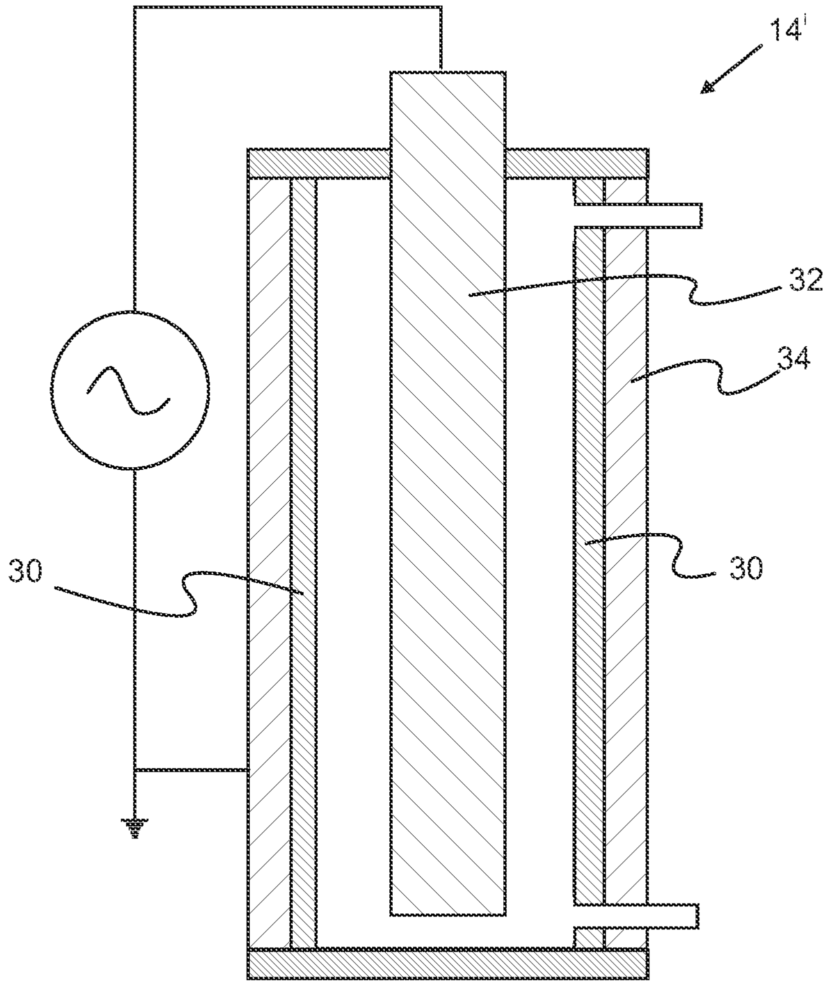
FIG. 2A. Longitudinal cross-section of dielectric barrier discharge plasma reactors.
Figure 2B:
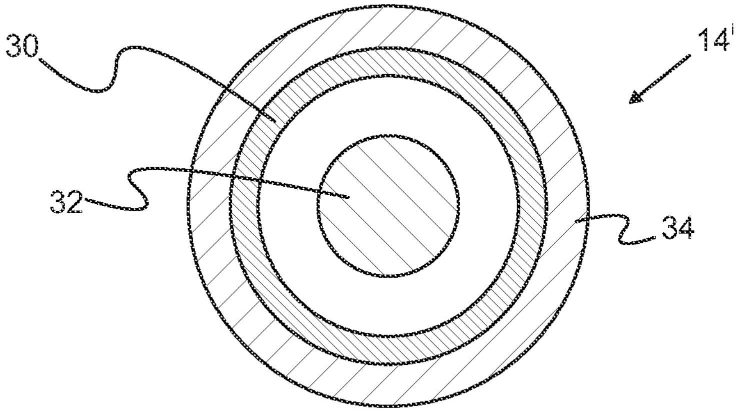
FIG. 2B. Cross-section of dielectric barrier discharge plasma reactors perpendicular to the cross-section of FIG. 2A.
Figure 3A:
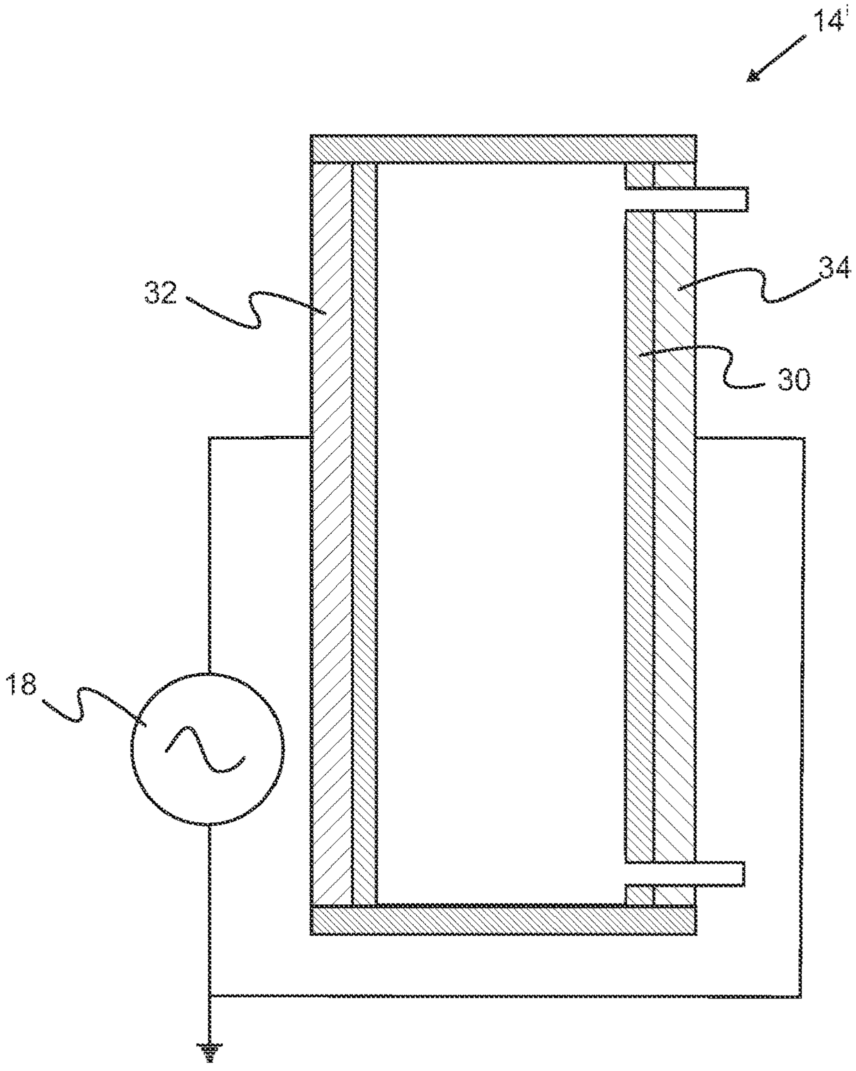
FIG. 3A. Longitudinal cross-section of dielectric barrier discharge plasma reactors.
Figure 3B:
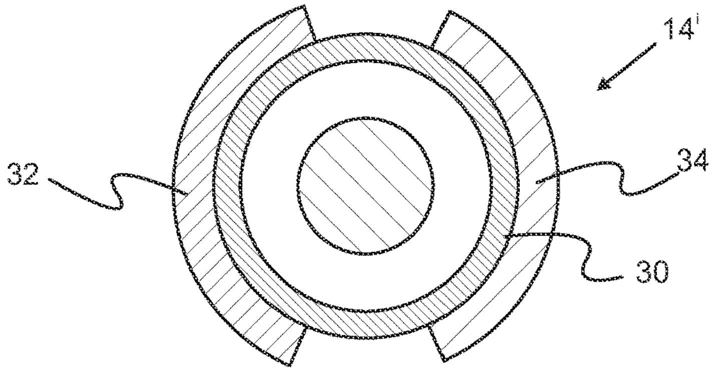
FIG. 3B. Cross-section of dielectric barrier discharge plasma reactors perpendicular to the cross-section of FIG. 3A.

In some variations, a dielectric barrier discharge plasma reactor includes a reaction tube (e.g., a quartz tube) and a pair of electrodes which are activated with an AC voltage to form an RF plasma that converts $CO_2$ to ethanol. FIGS. 2A, 2B, 3A, and 3B provide schematics of a design for a dielectric barrier discharge plasma reactor. Dielectric barrier discharge plasma reactors 14$^i$ includes a reaction tube 30 which is composed of a chemically inert dielectric material such as quartz. Although not limited by dimension, the reaction tube can have a diameter from about 2 to 4 cm and a length of 5 to 50 cm. Dielectric barrier discharge plasma reactors $14^i$ include a pair of electrodes 32 and 34. FIGS. 2A and 2B depict a variation in which electrode 32 is a central electrode placed within reaction tube 30 and electrode 34 is located on the outside of the reaction tube. In a refinement, electrode 34 is coated on the outside of reaction tube 30. FIGS. 3A and 3B depict a variation in which both electrodes 32 and 34 are located on the outside of reaction tube 30. In a refinement, electrodes 32 and 34 are coated on the outside of reaction tube 30. Power supply 18 provides the AC voltage across the electrodes as described below. In a refinement, power supply 18 is a negative power supply of 5-50 kV with an optional rectifier for the plasma generation. Multiple electrodes can be made of conduction metals such as stainless steel and nickel alloys.

In refinement, plasma reactor system 10 includes furnace 22 for heating the plurality 12 of dielectric barrier discharge (DBD) plasma reactors $14^i$. The reactors can be heated with clamp-shale furnace power with non-renewable or renewable electric sources. Alternatively, power produced at the site can also be used for heating the furnace. It should be appreciated that each reactor can be plasma generated with heating therein. Furnace can be used alone to generate a plasma or in combination with the dielectric barrier discharge (DBD) plasma reactors $14^i$.

In a variation, each DBD plasma reactor $14^i$ is packed with transition metal oxide catalyst. The catalyst can include a transition metal either supported or unsupported. The supports can include one metal oxide or a mixture of metal oxides. In a refinement, supports are oxides of p-block elements of the periodic table or hybrids such as zeolites, hydrotalcites or phosphor-silicates, activated carbon, and carbon nanotubes. In a refinement, the catalyst support includes a component selected from the group consisting of metal oxides, zeolites, hydrotalcites or phosphor-silicates, activated carbon, carbon nanotubes, and combinations thereof. Oxide supports may be acidic, neutral, or basic. Catalyst support with either oxygen storage capability or exhibiting redox property such as $CeO_2$ can also be used. Different loading of metal and supports weight ratio (0.1-100) can be used for specific applications. In a refinement, the catalysts are promoted with metal promoters or unpromoted.

For scale-up of the reactor configuration, a liner approach in parallel or series can be used that is already adapted in the industry. Therefore, a multi-tubular reactor system having 1-50 reactors is used for converting 60 $m^3/h$ ($5.08\times10^{-2}$ MSCFD) gas (e.g., $CO_2$) can be converted to high purity ethanol. Each tube can be loaded with 1 to 10 g of the catalyst. The catalyst can be reduced with a gas comprising of pure hydrogen or hydrogen gas diluted in an inert gas such as Ar, $N_2$, or He, which can be used. Also, other reducing gas such as CO may be used for the reduction of the catalyst prior to the plasma application. The rate of production of ethanol is about 1-10 μmol $gcat^{-1}$ $h^{-1}$ per tube.

Figure 4:
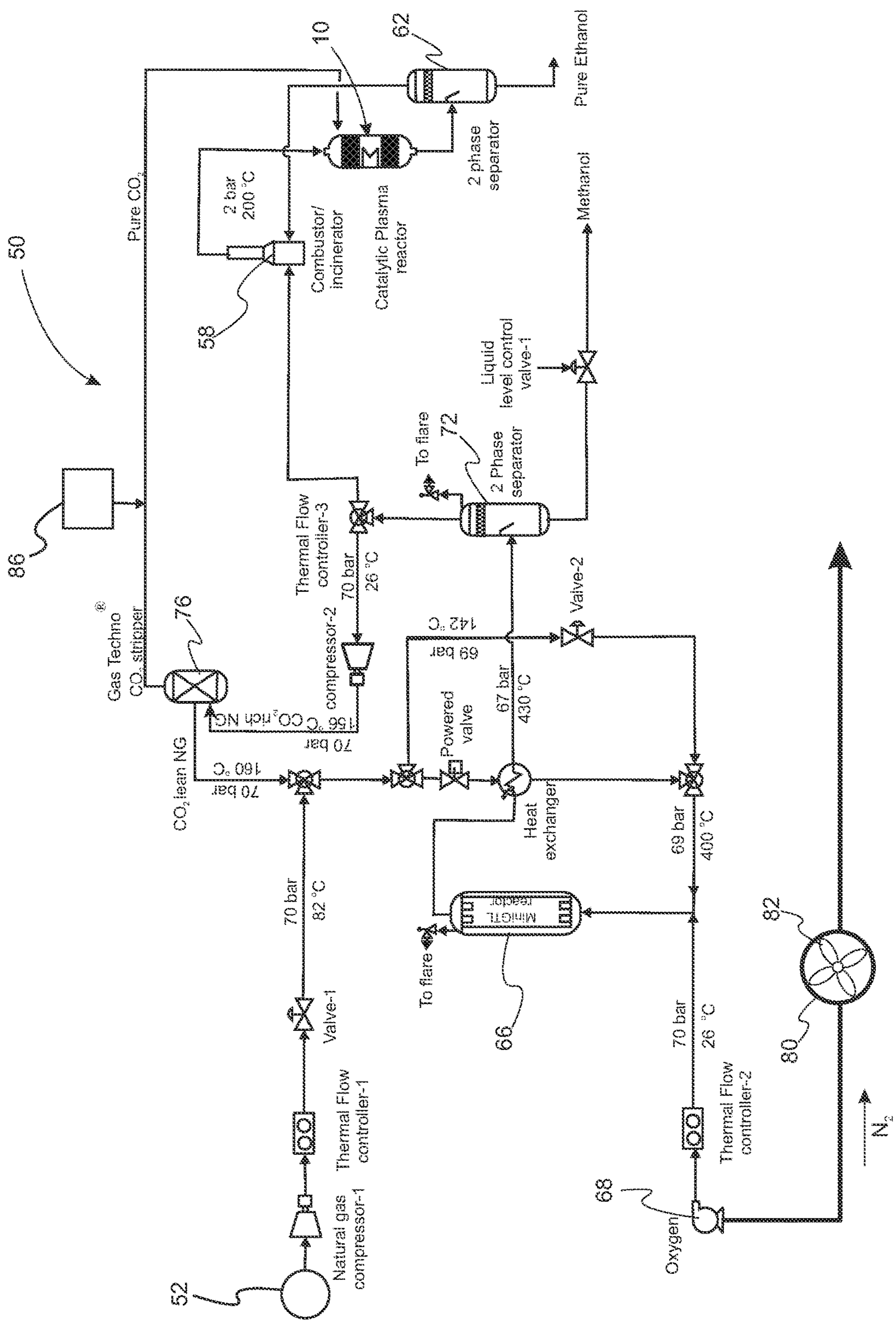
FIG. 4. GASTECHNO combined methanol and ethanol production scheme.

FIG. 4 provides a typical industrial reactor system that operate as $CO_2$ source 16 for to the plasma reactor system of FIG. 1. The reactor 50 depicted therein implements the GASTECHNO® combined methanol and ethanol production scheme. GASTECHNO® offers a unique way to produce methanol and ethanol from methane, ethane and varied feed gas compositions. Because of the modular design and high feed tolerance, the technology has been recognized internationally. GASTECHNO® system integrates plasma reactor system 10 described above in its modular design to produce additional ethanol by incorporating the DBD reactor while utilizing the stream that is either flared, vented, mechanically combusted and has a lower British thermal unit (BTU) fuel from its purge gas. This design reduces the net $CO_2$ footprint of any integrated landfill gas, digester gas, waste water treatment or associated gas upgrading process, and on top of that, the additional revenue generated from the production of ethanol will be produced from their waste streams.

Referring to FIG. 4, a gas stream of specific heat approximately 400-2000 BTU/pound can be used as a feed gas (source 52) for the synthesis of ethanol with and without pretreatment. A typical feed for the production of ethanol using a plasma reactor will need $CO_2$ and steam of any variable feed composition. Feed gas for the plasma reactor may comprise of $CO_2$:$H_2O$ in a molar ratio of about 1:2. The gas can be fed into the reactor either by pre-mixing or supplied from an independent source available at the site. 76

In a variation, the plasma reactor gas feed can be produced from the combination of inlet feed flared gas or a mechanically combusted vent stream at the GASTECHNO® site combined with all the $CO_2$ vents from other processes of pre-treatment and power generation along with the fuel purge gas source. In a refinement, rejected $CO_2$ from landfill gas or biogas is feed to the plasma reactor system. Prior to sending the gas to the plasma reactor, the combined gas is passed to a combustor/inclinator unit 58 where all the trace hydrocarbons will be combusted to produce a mixture of $CO_2$, $N_2$ and water vapor. The ratio of $CO_2$ and the steam water vapor can be balanced by a pure $CO_2$ stream and steam available at the site to meet the reaction stoichiometry of ~1:2 ($CO_2$:$H_2O$).

Further, the unconverted gas will be separated using a traditional gas-liquid separator 62. The flowsheet for the specific ethanol synthesis at the GasTehno® site is shown in FIG. 4. In a refinement, the $CO_2$-containing source includes a Mini-GTL reactor into which methane or natural gas is feed, and a mixture of gas comprising $CO_2$, methanol, and other unconverted feed gases is outputted. Therefore, the methane or natural gas stream from natural gas source 52 is fed into the Mini-GTL reactor 66 and either pre-mixed with an oxygen-containing gas or oxygen (i.e., $O_2$) in pure form.

In a refinement, oxygen is produced locally at oxygen station 68 and pre-mixed with natural gas. The reaction produces a mixture of gas comprising $CO_2$, methanol, and other unconverted feed gas stream. The methanol is purified in a sequence of separation units as illustrated by the 2-phase separator 72. Portion of the overhead gas from the 2-phase separator 72 is passed as purge gas to the incinerator unit 58 to combust unconverted hydrocarbons to produce mixture of $CO_2$ and water. The major fraction of the overhead gas from the 2-phase separator 72 is recycled back to reactor 66 optionally though $CO_2$ stripper 76 (e.g., a methanol scrubber). A useful methanol scrubber is disclosed in U.S. Pat. No. 9,180,426; the entire disclosure of which is hereby incorporated by reference in its entirety herein. Pure $CO_2$ can be collected from the recycle stream using the GASTECHNO® proprietary gas splitter 74 for $CO_2$ separation. The outlet stream of incinerator 58 includes the typical feed to be provided to the plasma reactor system 10. The pure $CO_2$ produced by the gas splitter 74 is used to balance the feed ratio of the plasma reactor. Unconverted gas is separated in a sequence of separators as depicted in FIG. 2 by the 2-phase separator downstream of the plasma reactor, and the unconverted overhead gas is recycled back to the inclinator 58. Pure ethanol is collected at the bottom of the 2-phase separator 62.

In a variation, oxygen station 68 outputs gaseous nitrogen with or without liquid nitrogen in addition to the oxygen used in reactor 50. The liquid nitrogen can be sold if desired. The gaseous nitrogen can be used to generate electricity via a flow-driven generator 80. In particular, the flow-driven generator 80 is operated by flow of the gaseous nitrogen stream to generate electricity. Typically, the flow-driven generator includes a flow-driven turbine 82. Characteristically, the nitrogen is at a pressure greater than 1 bar in order to rotate the turbine 82. In a refinement, the generated electricity is zero emissions and can be used in the operation of reactor 50 to make it more energy-efficient. An oxygen stream outputted from oxygen station 68 can be used in an industrial process using oxygen.

In another variation, reactor 50 is configured to receive addition $CO_2$-containing gas stream which are combined with the pure $CO_2$ stream. The reactor system of FIG. 5 is an example of such a reactor system having a $CO_2$ vent stream that can be combined with the pure $CO_2$ stream of reactor 50.

Figure 5:
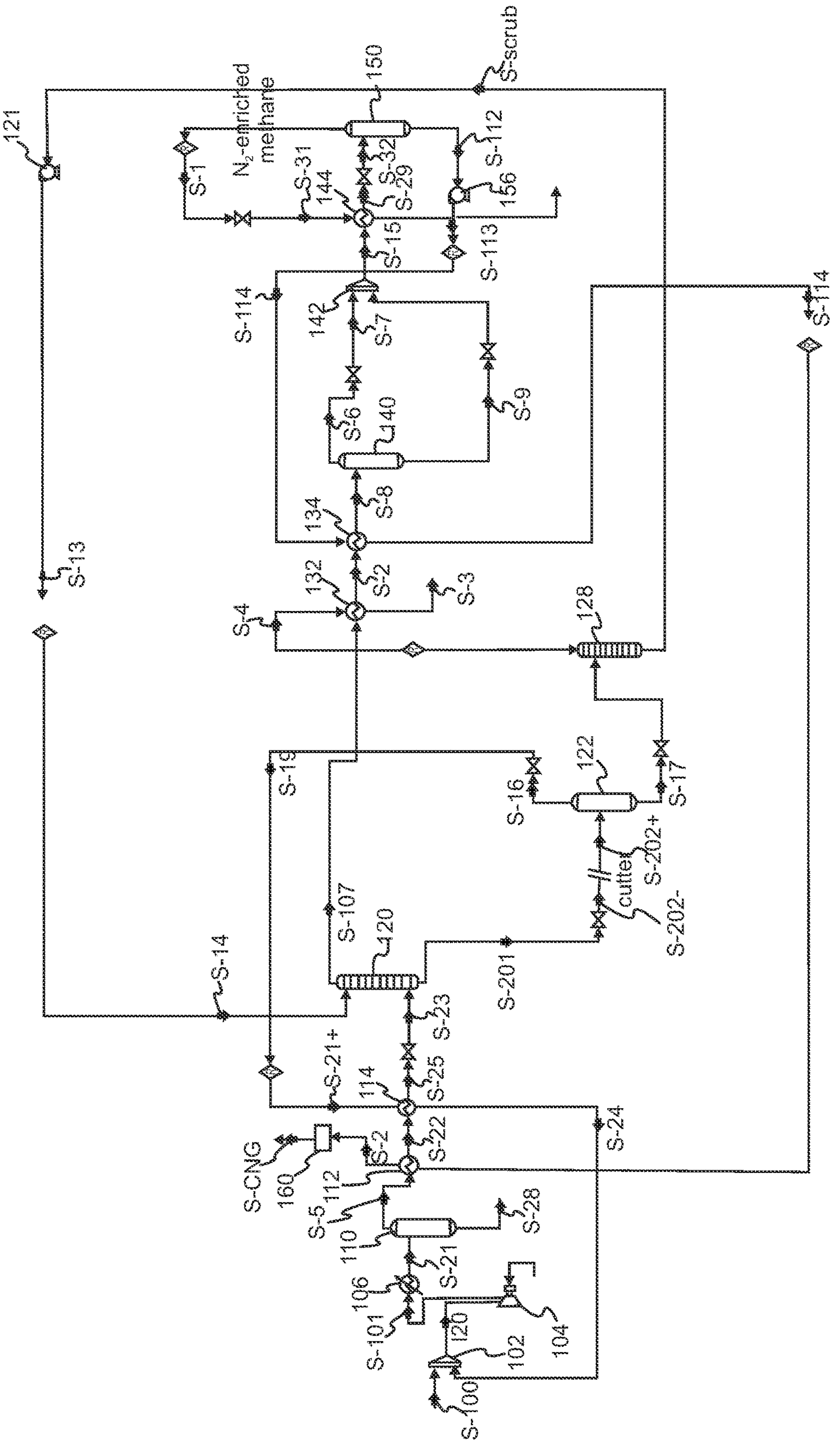
FIG. 5. Schematic of a reactor system that receives a $CO_2$-containing gas stream and outputs a $CO_2$ vent stream and a liquid natural gas stream.

FIG. 5 provides an example of industrial reactor system that can provide the $CO_2$ to the plasma reactor of FIG. 1. The industrial reactor system that includes a first stage that separates a discharge composition that includes carbon dioxide, hydrogen sulfide, and water from a methane-containing source gas stream and a second stage that produces liquid natural gas. Reactor system 100 receives as input source gas stream S-100. Table 1 set forth in FIGS. 6A-F provides physical and composition properties for various fluid streams in reactor system 100. The compositions of the stream are used in the method implemented by reaction system 100 that also produced $CO_2$ vent case to be supplied to the reactor 10 of FIG. 1. In a refinement, input source gas stream S-100 is obtained from a naturally occurring $CO_2$-containing gas such as landfill gas, biogas, digester gas, and the like. Source gas stream S-100 is received by mixer 102. Source gas stream S-100 includes methane, carbon dioxide, and optionally lower amounts of hydrogen sulfide, oxygen, nitrogen, and water as indicated in Table 1. In a refinement, recycled gas stream S-24 is combined with source gas stream S-100 is received by first mixer 102. Recycled gas stream S-24 can also include methane, carbon dioxide, and optionally, lower amounts of hydrogen sulfide, oxygen, nitrogen, and water. Gas stream S-20 emerges from mixer 102 and is compressed by compressor 104 to form compressed gas stream S-101 which is cooled by heat exchanger 106 to form gas stream S-21. Separator station 110 receives gas stream S-21. Separator station 110 separates first purified gas stream S-5 from liquid stream S-26. Advantageously, liquid stream S-26 includes water, carbon dioxide, and hydrogen sulfide. The separation is achieved by operating Separator station 110 at pressures from about 600 to 12 psia and temperature below 15° F. (e.g, from 1 to 15° F. with 8° F. being optimal). High pressure and cold temperatures. 800 psi, 8° F.

First purified gas stream S-5 is cooled by heat exchangers 112 and 114 to ultimately form second purified gas steam S-23. Water/methanol scrubber 120 removes carbon dioxide, and hydrogen sulfide from second purified gas stream S-23 to form third purified gas stream S-107 which includes greater than 80 mole percent methane and less than 10 mole percent nitrogen gas. In this regard, methanol-water liquid stream S-14 is provided to methanol/water scrubber 120 to perform the scrubbing.

Discharge liquid stream S-201 from water/methanol 120 includes methanol, water, carbon dioxide, and methane in an amount less than 5 mole percent. The methane in discharge stream S-201 can be purified in gas-liquid separator 122 to form fourth purified stream S-16 which is recycled back to mixer 102. Liquid gas steam S-17 which is separated from discharge stream S-201 by gas-liquid separator 122 includes predominantly methanol (i.e., greater than 50 mole percent) and carbon dioxide. Flash drum 128 removes carbon dioxide as a vent gas stream S16 which passes through heat exchanger 132 to form vent carbon dioxide-containing gas stream S-3. Advantageously, vent carbon dioxide-containing stream S-3 ($CO_2$ vent gas) can be supplied to the reactor 10 above to form ethanol. Methanol-containing gas stream S-scrub is obtained from flash drum 128 and then recycled back to water scrubber 120 via pump 121. Methanol-containing liquid stream S-scrub includes both methanol and water each in amounts typically over 40 mole percent.

Methane-containing stream S-107 which as noted above is obtained from methanol/water scrubber 120 is cooled by flowing through heat exchanges 132 and 134 to form first methane-containing stream S-8. Gas-liquid separator 140 separates methane-containing gas stream S-6 and first methane-containing liquid stream S-9 from methane-containing stream S-107.

Second mixer 142 recombines methane-containing vapor stream S-6 and methane-containing liquid stream S-9 to form second methane-containing liquid stream S-15. Second methane-containing liquid stream S-15 passes through heat exchanger 142 to form third methane-containing liquid stream S-32 (after passing through a valve). Gas-liquid separator 150 separates $N_2$-enriched gas stream S-rich and methane-containing liquid stream S-112 from methane-containing liquid stream S-32. This separation is achieved by operating gas-liquid separator 150 below the boiling point of methane (e.g., temperatures below −260° F.) methane-containing liquid stream S-112 can be pumped out by LNG pump 152 as a product stream liquid methane stream S-114. In a variation, stream liquid methane stream S-114 can be vaporized in vaporizer 160 to form compressed natural gas stream S-CNG which can be stored and transported.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

REFERENCES

[1] H. Al Baroudi, A. Awoyomi, K. Patchigolla, K. Jonnalagadda, and E. J. Anthony, "A review of large-scale $CO_2$ shipping and marine emissions management for carbon capture, utilisation and storage," *Appl. Energy*, vol. 287, no. December 2020, p. 116510, 2021, doi: 10.1016/j.apenergy.2021.116510.

[2] "IPCC Fifth Assessment Report." https://www.ipcc.ch/assessment-report/ar5/.

[3] H. Xu et al., "Highly selective electrocatalytic $CO_2$ reduction to ethanol by metallic clusters dynamically formed from atomically dispersed copper," *Nat. Energy*, vol. 5, no. 8, pp. 623-632, 2020, doi: 10.1038/s41560-020-0666-x.

What is claimed is:

1. A plasma reactor system for producing ethanol from carbon dioxide comprising:

one or more dielectric barrier discharge plasma reactors, each of the one or more dielectric barrier discharge plasma reactors being packed with a transition metal oxide catalyst, the transition metal oxide catalyst comprising $Cu/Zn/Al_2O_3$, wherein the one or more dielectric barrier discharge plasma reactors are configured to receive a plasma reactor gas feed from a $CO_2$-containing source, the plasma reactor gas feed comprising a mixture of $CO_2$ and $H_2O$ and to output ethanol.

2. The plasma reactor system of claim 1, wherein the $CO_2$-containing source is an industrial reactor or a naturally occurring source.

3. The plasma reactor system of claim 1, wherein each dielectric barrier discharge plasma reactor of the one or more dielectric barrier discharge plasma reactors includes a reaction tube that is composed of a chemically inert dielectric material.

4. The plasma reactor system of claim 3, wherein the reaction tube is composed of quartz.

5. The plasma reactor system of claim 1, wherein the transition metal oxide catalyst includes a transition metal that is either supported or unsupported.

6. The plasma reactor system of claim 5, wherein the transition metal oxide catalyst includes a catalyst support.

7. The plasma reactor system of claim 6, wherein the catalyst support includes a component selected from the group consisting of metal oxides, zeolites, hydrotalcites or phosphor-silicates, activated carbon, carbon nanotubes, and combinations thereof.

8. The plasma reactor system of claim 6, wherein the catalyst support exhibits oxygen storage capacity and/or redox properties.

9. The plasma reactor system of claim 6, wherein a weight ratio of the transition metal to support is from 0.1 to 100.

10. The plasma reactor system of claim 1, wherein a plasma is generated in each plasma reactor thermally or non-thermally generated.

11. The plasma reactor system of claim 1, wherein each of the one or more dielectric barrier discharge plasma reactors includes a pair of electrodes for generating an RF plasma.

12. The plasma reactor system of claim 1, further comprising a furnace for heating the one or more dielectric barrier discharge plasma reactors.

13. The plasma reactor system of claim 1, wherein a molar ratio of $CO_2$ to $H_2O$ is about 1:2.

14. The plasma reactor system of claim 1, wherein the $CO_2$-containing source is an industrial reactor produced methanol, ethanol, or combinations thereof.

15. The plasma reactor system of claim 14, wherein the plasma reactor gas feed is produced from a combination of inlet feed flared gas and a fuel purge gas source.

16. The plasma reactor system of claim 15, wherein prior to sending the gas to the plasma reactor system, the combination of inlet feed flared gas, and the fuel purge gas source is passed to a combustor/inclinator unit where traces of hydrocarbons are combusted to produce a mixture of $CO_2$, $N_2$, and water vapor.

17. The plasma reactor system of claim 16, wherein unconverted gas is separated using a gas-liquid separator.

18. The plasma reactor system of claim 14, wherein the $CO_2$-containing source includes a Mini-GTL reactor into which methane or natural gas is feed, and a mixture of gas comprising $CO_2$, methanol, and other unconverted feed gases is outputted.

19. The plasma reactor system of claim 18, wherein oxygen is produced locally at an oxygen station and premixed with natural gas.

20. The plasma reactor system of claim 19, wherein methanol is purified in a sequence of separation units that include a 2-phase separator.

21. The plasma reactor system of claim 20, wherein a portion of overhead gas from the 2-phase separator is passed to an incinerator unit to combust unconverted hydrocarbons to produce a mixture of $CO_2$ and water.

22. The plasma reactor system of claim 21, wherein a major fraction of overhead gas from the 2-phase separator is recycled back to the Mini-GTL reactor as a recycle stream.

23. The plasma reactor system of claim 22, wherein pure $CO_2$ is collected from the recycle stream using a gas splitter for $CO_2$ separation.

24. The plasma reactor system of claim 23, wherein pure $CO_2$ produced by the gas splitter for $CO_2$ separation is used to balance a feed ratio of the plasma reactor system.

25. The plasma reactor system of claim 23, wherein rejected $CO_2$ from landfill gas or biogas is feed to the plasma reactor system.

26. The plasma reactor system of claim 19, wherein the oxygen station outputs gaseous nitrogen with or without liquid nitrogen in addition to oxygen used in an industrial reactor.

27. The plasma reactor system of claim 26, wherein the gaseous nitrogen is used to generate electricity via a flow-driven generator.

28. The plasma reactor system of claim 27, wherein the flow-driven generator includes a flow-driven turbine.

29. The plasma reactor system of claim 1, wherein the $CO_2$-containing source is an industrial reactor system that includes a first stage and a second stage, the first stage separating a discharge stream and a purified methane-containing gas stream from an input from a methane-containing source gas stream, the discharge stream including carbon dioxide, hydrogen sulfide, and water and the second stage producing liquid natural gas purified methane-containing gas from the purified methane-containing gas stream.

30. The plasma reactor system of claim 29, wherein the first stage includes gas-liquid separator that separates $CO_2$ from the discharge stream.

31. The plasma reactor system of claim 29, wherein the second stage includes a gas-liquid separator that separates liquid methane from the purified methane-containing gas stream.

* * * * *